(12) United States Patent
Avella et al.

(10) Patent No.: US 7,411,044 B2
(45) Date of Patent: *Aug. 12, 2008

(54) POLYMERIZED HEMOGLOBIN SOLUTIONS HAVING REDUCED AMOUNTS OF TETRAMER AND METHOD FOR PREPARING

(75) Inventors: Anthony Avella, Crystal Lake, IL (US); Richard DeWoskin, St. Charles, IL (US); Marc Doubleday, Cary, IL (US)

(73) Assignee: Northfield Laboratories, Inc., Evanson, IL (US)

( * ) Notice: Subject to any disclaimer, the term of this patent is extended or adjusted under 35 U.S.C. 154(b) by 104 days.

This patent is subject to a terminal disclaimer.

(21) Appl. No.: 11/509,454

(22) Filed: Aug. 24, 2006

(65) Prior Publication Data

US 2006/0287222 A1 Dec. 21, 2006

Related U.S. Application Data

(63) Continuation of application No. 10/767,516, filed on Jan. 29, 2004, now Pat. No. 7,135,553.

(60) Provisional application No. 60/443,436, filed on Jan. 29, 2003.

(51) Int. Cl.
*A61K 35/14* (2006.01)
*A61K 38/16* (2006.01)
*C07K 14/00* (2006.01)

(52) U.S. Cl. .................. 530/385; 530/402; 530/412; 530/414; 530/418; 530/427; 530/829; 424/529; 424/533; 514/6; 514/832

(58) Field of Classification Search .............. 530/385, 530/402, 412, 414, 418, 427, 829; 424/529, 424/533; 514/6, 832
See application file for complete search history.

(56) References Cited

U.S. PATENT DOCUMENTS

| | | | |
|---|---|---|---|
| 4,001,200 A | 1/1977 | Bonsen et al. |
| 4,001,401 A | 1/1977 | Bonsen et al. |
| 4,049,673 A | 9/1977 | Scheinberg |
| 4,053,590 A | 10/1977 | Bonsen et al. |
| 4,061,736 A | 12/1977 | Morris et al. |
| 4,113,853 A | 9/1978 | Funakoshi et al. |
| 4,136,093 A | 1/1979 | Bonhard et al. |
| 4,485,174 A | 11/1984 | Chiang et al. |
| 4,526,715 A | 7/1985 | Kothe et al. |
| 4,529,719 A | 7/1985 | Tye |
| 4,650,786 A | 3/1987 | Wong |
| 4,711,852 A | 12/1987 | Jacobson et al. |
| 4,761,209 A | 8/1988 | Bonaventure et al. |
| 4,826,811 A | 5/1989 | Sehgal et al. |
| 4,835,097 A | 5/1989 | Saunders |
| 4,857,636 A | 8/1989 | Hsia |
| 4,861,867 A | 8/1989 | Estep |
| 5,028,588 A | 7/1991 | Hoffman et al. |
| 5,061,688 A | 10/1991 | Beissinger et al. |
| 5,084,558 A | 1/1992 | Rausch et al. |
| 5,194,590 A | 3/1993 | Sehgal et al. |
| 5,206,075 A | 4/1993 | Hodgson, Jr. |
| 5,217,648 A | 6/1993 | Beissinger et al. |
| 5,241,031 A | 8/1993 | Mehta |
| 5,272,236 A | 12/1993 | Lai et al. |
| 5,278,272 A | 1/1994 | Lai et al. |
| 5,296,465 A | 3/1994 | Rausch et al. |
| 5,380,824 A | 1/1995 | Marschall et al. |
| 5,438,041 A | 8/1995 | Zheng et al. |
| 5,464,814 A | 11/1995 | Sehgal et al. |
| 5,691,452 A | 11/1997 | Gawryl et al. |
| 5,691,453 A | 11/1997 | Wirtz et al. |
| 5,695,840 A | 12/1997 | Mueller |
| 5,747,649 A | 5/1998 | Sehgal et al. |
| 5,789,376 A | 8/1998 | Hsia |
| 5,840,852 A | 11/1998 | Rausch et al. |
| 5,895,810 A | 4/1999 | Light et al. |
| 5,929,031 A | 7/1999 | Kerwin et al. |
| 5,955,581 A | 9/1999 | Rausch et al. |
| 5,988,422 A | 11/1999 | Vallot |
| 5,998,361 A | 12/1999 | Bucci et al. |
| 6,027,776 A | 2/2000 | Mueller |
| 6,076,457 A | 6/2000 | Vallot |
| 6,133,425 A | 10/2000 | Sehgal et al. |
| 6,150,507 A | 11/2000 | Houtchens et al. |
| 6,271,351 B1 | 8/2001 | Gawryl et al. |
| 6,288,027 B1 | 9/2001 | Gawryl et al. |
| 6,323,320 B1 | 11/2001 | Sehgal et al. |
| 6,498,141 B2 | 12/2002 | DeWoskin et al. |
| 6,552,173 B2 | 4/2003 | Sehgal et al. |
| 7,135,553 B2 * | 11/2006 | Avella et al. ............ 530/385 |
| 2002/0065211 A1 | 5/2002 | Jacobs, Jr. et al. |

FOREIGN PATENT DOCUMENTS

| | | |
|---|---|---|
| EP | 0 361 720 A | 4/1990 |
| WO | WO 97/35883 | 10/1997 |
| WO | WO 00/21366 | 4/2000 |

OTHER PUBLICATIONS

Gould, S.A., et al., *The Life-Sustaining Capacity of Human Polymerized Hemoglobin when Red Cells Might Be Unavaiable*, Journal of the American College of Surgeons, 195 (4):445-455 (Oct. 2002).

(Continued)

*Primary Examiner*—Jon P Weber
*Assistant Examiner*—Abdel A Mohamed
(74) *Attorney, Agent, or Firm*—McDonnell Boehnen Hulbert & Berghoff LLP

(57) ABSTRACT

A substantially tetramer free hemoglobin solution and a method for producing a substantially tetramer free hemoglobin solution. The method includes polymerizing a solution of hemoglobin, treating the polymerized hemoglobin solution to partially degrade the polymer to tetramer and removing tetramer from the hemoglobin solution.

30 Claims, 10 Drawing Sheets

OTHER PUBLICATIONS

Carson, J.L., et al., *Mortality and morbidity in patients with very low postoperative Hb levels who decline blood transfusion*, Transfusion, 42: 812-818 (Jul. 2002).

Moore, F.A., et al., *Trauma Resuscitation*, ACS Surgery-Principles & Practice, 31-61 (2002).

American College of Surgeons Committee on Trauma. Advanced Trauma Life Support Program for Physicians 1997 Instructional Manual, 6th, ed. Chicago: American College of Surgeons; 98-117 (1997).

Farion, K.J., et al., *Changes in Red Cell Transfusion Practice among Adult Trauma Victims*, J. Trauma, 44(4):583-587 (1998).

Baker, J.B., et al., *Type and Crossmatch of the Trauma Patient*, J. Trauma, 50(5):878-881 (May, 2001).

DeFoe, G.R., et al., *Lowest Hematocrit on Bypass and Adverse Outcomes Associated with Coronary Artery Bypass Grafting*, Ann Thorac Surg., 71:769-776 (2001).

Wu, W.C., et al., *Blood Transfusion in Elderly Patients with Acute Miyocardial Infarction*, New England Journal of Medicine, 345(17):1230-1236 (Oct. 2001).

Practice Guidelines for Blood Component Therapy: A report by the American Society of Anesthesiologists Task Force on Blood Component Therapy, Anesthesiology 84(3):732-747 (Mar. 1996).

Consensus Conference. Perioperative Red Blood Cell Transfusion, JAMA 260(18): 2700-2703 (Nov. 1988).

Gould, S.A., et al., *Fluosol DA-20 As A Red Cell Substitute in Acute Anemia*, New England Journal of Medicine, 314(26):1653-1656 (Jun. 1986).

Spence, R.K., et al., *Fluosol DA-20 in the treatment of severe anemia: Randomized, controlled study of 46 patients*, Critical Care Medicine, 18(11):1227-1230 (Nov. 1990).

Spence, R.K., et al., *Is Hemoglobin Level Alone a Reliable Predictor of Outcome in the Severely Anemic Patient?* The American Surgeon, 58(2):92-95 (1992).

Carson, J.L., et al., *Severity of Anaemia and Operative Mortality and Morbidity*, Lancet 1(8588):727-729 (Apr. 1988).

Carson, J.L., et al., *Effect of anaemia and cardiovascular disease on surgical mortality and morbidty*, Lancet, 348(9034):1055-1060 (Oct. 1996).

Viele, M.K., et al., *What can we learn about the need for transfusion from patients who refuse blood? The experience with Jehovah's Witnesses*, Transfusion 34(5):396-401 (1994).

Sehgal L.R., et al., *Polymerized pyridoxylated hemoglobin: A red cell substitute with normal oxygen capacity*, Surgery 95:433-438 (1984).

Amberson, W.R., et al., *Clinical Experience with Hemoglobin-Saline Solutions*, J. Applied Physiology, 1(7):469-489 (Jan. 1949).

Brandt, J.L., et al., *The Effects of Hemoglobin Solutions on Renal Functions in Man*, Blood, 6:1152-1158 (1951).

Miller, J.H., et al., *The Effect of Hemoglobin on Renal Function in The Human*, Journal of Clinical Investigation, 30:1033-1040 (Jul. 1951).

Savitsky, J.P., et al., *A clinical trial of stroma-free hemoglobin*, Clinical Phamacology Journal, 23(1):73-80 (Jan. 1978).

Carmichael, F.J., et al., *A phase I study of oxidized raffinose crosslinked human hemoglobin*, Crit Care Med., 28(7):2283-2292 (2000).

Kasper, S.M., et al., *Effects of a Hemoglobin-Based Oxygen Carrier (HBOC-201) on Hemodynamics and Oxygen Transport in Patients Undergoing Preoperative Hemodiulution for Elective Abdominal Aortic Surgery*, Anesth Analg, 83:921-927 (1996).

LaMuraglia, G.M., et al., *The reduction of the allogenic transfusion requirement in aortic surgery with a hemoglobin-based solution*, J. Vascular Surgery, 31(2):299-308 (Feb. 2000).

Sloan, E.P., et al., *Diaspirin Cross-Linked Hemoglobin (DCLHb) in the Treatment of Severe Traumatic Hemorrhagic Shock*, JAMA 282:1857-1864 (Nov. 1999).

Gould, S.A., et al., *Clinical Utility of Human Polymerized Hemoglobin as a Blood Substitute AfterAcute Ttrauma and Urgent Surgery*, J. Trauma 43(2):325-332 (Aug. 1997).

Gould, S.A., et al., *The First Randomized Trial of Human Polymerized Hemoglobin as a Blood Substitute in Acute Trauma and Emergent Surgery*, J Am Coll Surg 187(2):113-122 (Aug. 1998).

Vengelen-Tyler, V., American Association of Blood Banks Technical Manual. 13th ed., Bethesda (MD): American Association of Blood Banks, p. 389-396 (1999).

Huston, P., et al., *Withholding Proven Treatment in Clinical Research*, New England Journal of Medicine 345(12):912-914 (Sep. 2001).

Emanuel, E.J., et al., *The Ethics of Placebo-Controlled Trials- A Middle Ground*, New England Journal of Medicine, 345(12):915-914 (Sep. 2001).

Carson, J.L, et al., *Mortality and morbidity in patients with very low blood counts who decline blood transfusion*, Transfusion, 42:812-818 (Jul. 2002).

Reiner, A.P., *Massive Transfusion*, Perioperative Transfusion Medicine, p. 351-364 (1998).

Weiskopf, R.B., et al., *Human Cardiovascular and Metabolic Response to Acute, Severe Isovolemic anemia*, JAMA 279(3): 217-221 (Jan. 1998).

Wilkerson, D.K., et al., *Limits of cardiac compensation in anemic baboons*, Surgery, 103(6):665-670 (1988).

Levy, P.S., et al., *Oxygen Extraction Ratio: A Valid Indicator of Transfusion Need in a Limited Coronary Vascular Reserve?* J. Trauma 32(6):769-774 (Jun. 1992).

Schwartz, J.P., et al., *The Influence of Coronary Stenosis On Transfusion Need*., Cardiothoracic Surgery, Surgical Forum XLIV:226-228 (1993).

Moss, G.S., et al., *Transport of Oxygen and Carbon Dioxide by Hemoglobin-Saline Solution in the Red Cell-Free Primate*, Surg. Gynecol Obstet, 142:357-362 (Mar. 1976).

Frantantoni, J.C., *Points to consider on efficacy evalution of hemoglobin and perfluoracarbon based oxygen carriers*, Transfusion 34(8):712-713 (1994).

Frantantoni, J.C., *Red Cell Subsittutes: Evolution of Approaches for Demonstrating Efficacy*, Blood-substitutes—Present and Future Perspectives, Elsevier Science S.A., p. 33-39 (1998).

Sehgal, L.R. et al., *Preparation and in vitro characteristics of polymerized pyridoxylated hemoglobin*, Transfusion, 23(2):158-162 (1983).

Sharma, A., et al., *An Isologous Procine Promoter Permits High level Expression of Human Hemoglobin in Transgenic Swine*, Biotechnology, 12:55-59 (1994).

Looker, D., et al., *A human recombinant haemoglobin designed for use as a blood substitute*, Nature, 356-258-260 (1992).

* cited by examiner

US 7,411,044 B2

POLYMERIZED HEMOGLOBIN SOLUTIONS HAVING REDUCED AMOUNTS OF TETRAMER AND METHOD FOR PREPARING

CROSS REFERENCE TO RELATED APPLICATION

This application is a continuation of U.S. Ser. No. 10/767,516, filed Jan. 29, 2004, now U.S. Pat. No. 7,135,553, which claims the benefit of U.S. Provisional Application Ser. No. 60/443,436, filed Jan. 29, 2003.

FIELD OF THE INVENTION

The invention relates to stabilized oxygen carrying solutions. More specifically, it relates to hemoglobin solutions that have been treated to enhance polymer bond stability and to remove tetramer that has been elaborated.

BACKGROUND OF THE INVENTION

There is a consistent need for ready blood products for an ever-increasing surgical and trauma load, and to supplement blood bank shortages. Oxygen carrying solutions, such as hemoglobin-derived solutions can be used in place of whole blood or red blood cells for patients having a need for augmented oxygen carrying capacity. Because they are not dependent upon donor availability, such solutions can be made readily available in an emergency situation or during a blood bank shortage. Also, due to risk of infection of blood borne pathogens as a result of a blood transfusion, a patient may prefer a hemoglobin-derived solution for transfusion in place of whole blood or red blood cells. In particular, such solutions may include, but are not limited to, oxygen carriers, blood substitutes, and hemoglobin-derived compositions such as those disclosed in U.S. Pat. Nos. 6,498,141, 6,133,425, 5,464,814, 5,438,041, 5,217,648, 5,194,590, 5,061,688, and 4,826,811, the teachings of which are incorporated herein by reference in their entirety.

Stroma-free hemoglobin is known in the art to have oxygen transport and reversible oxygen (or ligand) binding capacities. However, hemoglobin solutions, while capable of carrying sufficient quantities of oxygen to support life, have presented challenges because of several undesirable side effects such as a decrease in kidney performance. These effects were thought to be due to the presence of unwanted contaminants such as bacterial endotoxin or fragments of red cell membranes (stroma) that is not removed from solution. While contaminants such as these can indeed produce renal alterations, hemoglobin solutions essentially free of such contaminants still produce substantial renal dysfunction. The cause for the renal dysfunction can be ascribed to, among other things, physiologically unacceptable amounts of unpolymerized hemoglobin tetramer.

Essentially tetramer free hemoglobin solutions can be used to replenish essentially all of a human patient's blood volume without causing vasoconstriction, renal toxicity, hemoglobinuria or other problems associated with intravenous administration of synthetic or semisynthetic oxygen carriers and blood substitutes. While these solutions provide superior efficacy, the shelf life of the product is limited since the hemoglobin polymer is known to slowly degrade to tetrameric units over time. Accordingly, what is needed is a method for maintaining the solution as a substantially tetramer free solution for an extended period to increase the shelf life of the solution.

SUMMARY OF THE INVENTION

In one aspect, the invention provides a method for producing a substantially tetramer free hemoglobin solution comprising polymerizing hemoglobin in solution, treating the polymerized hemoglobin to elaborate tetramer and removing tetramer from the polymerized hemoglobin solution.

In another aspect, the invention relates to a substantially tetramer free hemoglobin solution produced by polymerizing a solution of hemoglobin, heat treating the polymerized hemoglobin solution to elaborate tetramer, and removing tetramer from the polymerized hemoglobin solution.

In a further aspect, the invention relates to a method for stabilizing a polymerized hemoglobin solution comprising treating the polymerized hemoglobin solution to partially degrade the polymerized hemoglobin to tetramer and removing tetramer from the solution.

In yet another aspect, the invention provides a method for producing a stabilized, polymerized hemoglobin solution. The method includes producing a polymerized hemoglobin solution, removing tetramer from the polymerized hemoglobin solution to produce a substantially tetramer free polymerized hemoglobin solution, aging the polymerized hemoglobin solution to allow tetramer to elaborate, and removing the elaborated tetramer. The aging may include storing the hemoglobin solution until the tetramer concentration is greater than about 1.0% of total hemoglobin, such as longer than one year.

The hemoglobin may be derived from mammalian blood, such as human or bovine blood. The hemoglobin may be polymerized with glutaraldehyde. The tetramer may be removed by filtration. The treatment of the polymerized solution to elaborate tetramer may be accomplished by heating the solution above about 45° C. for at least about 24 hours. The tetramer concentration after removing tetramer may be less than about 1.0% of total hemoglobin in the solution, or less than about 0.3% of total hemoglobin in the solution.

DETAILED DESCRIPTION

Figure 1:
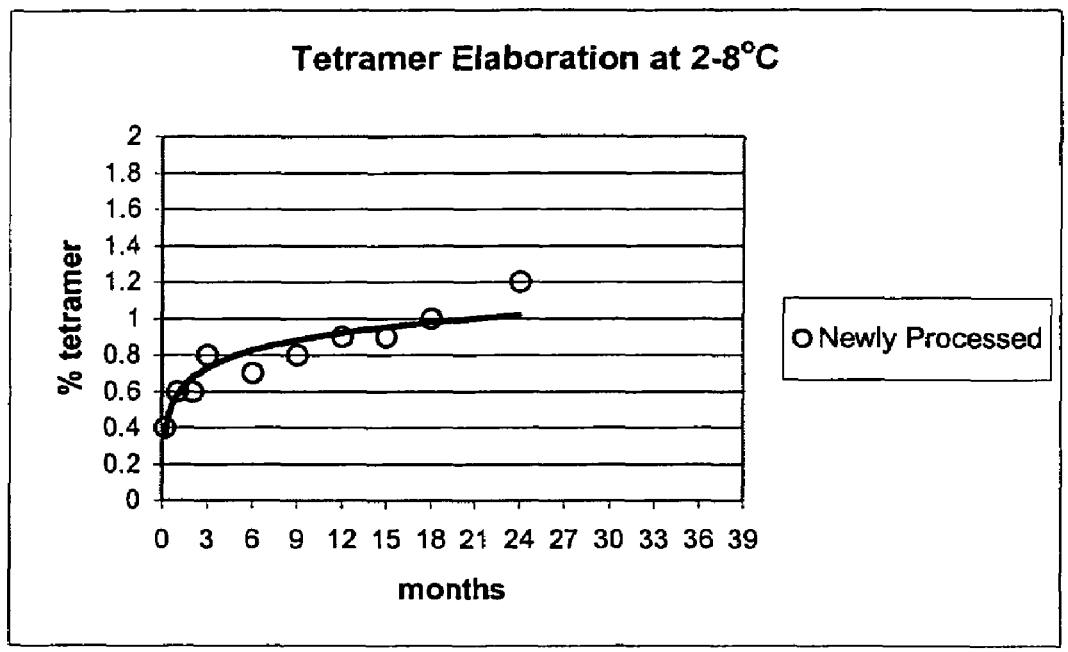
FIG. 1 shows the amount of tetramer elaboration in hemoglobin solutions stored at 2-8° C.

The invention provides an oxygen carrying solution comprising an essentially tetramer-free, cross-linked, polymerized, hemoglobin which is substantially free of stroma, stromal contaminants and other contaminants.

Before describing the present invention in detail, a number of terms will be defined. It is to be understood that the terminology used herein is for the purpose of describing particular embodiments only, and is not intended to be limiting. As used herein, the singular forms "a," "an," and "the" include plural referents unless the context clearly dictates otherwise.

"Hemoglobin" refers to hemoglobin derived from any source. Hemoglobin may be derived from mammals including humans, cattle, pigs, and sheep, or from other sources such as transgenically-produced hemoglobin described in BIO/TECHNOLOGY, 12: 55-59 (1994), and recombinantly produced hemoglobin, such as the recombinantly produced hemoglobin described in Nature, 356: 258-260 (1992). As used herein, % total hemoglobin (THb) is defined as grams of hemoglobin/100 mL of solution.

A "solution of hemoglobin" refers to a solution of tetrameric or polymerized hemoglobin molecules where the molecules are not contained within a red blood cell. Such a solution need not be free of or substantially free of red blood cell stroma or stromal contaminants. However, in one aspect of the invention, solutions of polymerized hemoglobin are substantially free of red blood cell stroma and stromal contaminants.

"Cross-linked" means the chemical placement of molecular "bridges" onto or into a molecule, or between molecules with the purpose of altering the shape, size, function or physical characteristics of the molecule. Cross-linked molecules may be polymerized or non-polymerized, i.e., cross-linked molecules may be tetrameric.

"Tetramer" or "tetrameric" refers to hemoglobin molecules having a molecular weight of about 64 Kd; that is, the term refers to both native and intramolecularly crosslinked hemoglobin molecules. As used herein % tetramer refers to the amount of tetramer as a percentage of the amount of total hemoglobin (THb) in solution. For example, a 100 mL hemoglobin solution having 10% THb and 1% tetramer has 0.1 g tetramer in solution.

"Essentially tetramer free" denotes the level of purity with respect to tetramer contamination at which certain biological responses to tetramer administered into a mammal are no longer present. A main criterion is the absence of alterations in renal function when pharmaceutically effective amounts are infused, that is, at a level of purity of about 99% or better (less than about 1% of tetramer is present). The preferred product produced by the inventive process contains no more than about 0.8% tetramer based on the weight of total hemoglobin (THb). In other words, an essentially tetramer-free product according to the invention contains no more then physiologically acceptable amounts of unpolymerized hemoglobin tetramer. Particularly preferred products of the invention contain less than about 0.5% tetramer; the most particularly preferred products of the invention contain about 0.3-0.4% tetramer. Such amounts of tetramer have been found to be physiologically acceptable.

"Elaboration" or "tetramer elaboration" refers to an increase of the amount of tetramer in solution due to the degradation of polymerized hemoglobin to tetramer. Degradation of the polymer can be the result of treatment with chemicals, temperature, time or a combination thereof. Generally, tetramer elaborates upon heating or as the polymerized solution ages. Thus, percent tetramer increases during storage of the solution. Tetramer elaboration can be accelerated by heating the polymerized hemoglobin solution. Elaboration is said to have occurred after any increase in the amount of tetramer in solution. As used herein, the partial degradation of a polymerized hemoglobin refers to some, but not all, of the polymer in solution being degraded to tetramer.

"Aging" a hemoglobin solution refers to storing the solution for any amount of time at any temperature. Higher temperatures accelerate the effects of aging on the hemoglobin solution. An "aged" hemoglobin solution has been stored so that tetramer has elaborated.

"Pre-elaboration" or "tetramer pre-elaboration" refers to a technique that utilizes heat treatment to promote tetramer elaboration.

"Hot quench" refers to a processing technique that involves heating the solution during the polymerization quench reaction to drive the reaction to completion.

"Polymerizing" or "Polymerized" means the act of, or the result of, the placement of molecular bridges between molecules or tetrameric subunits where the size and weight of the resulting polymerized molecule is increased with respect to native or tetrameric hemoglobin. Polymerized hemoglobin is not tetrameric hemoglobin. Polymerization may be accomplished using various polymerizing agents, including glutaraldehyde, imido esters, or others, in a biochemically suitable carrier, as is well known to those skilled in the art.

"Pyridoxylated" or "pyridoxylation" refers to the method of, or the result of, binding pyridoxal-5'-phosphate containing molecules to a hemoglobin molecule by reacting the molecule with pyridoxal-5'-phosphate ("P5P") or 2-Nor-formyl pyridoxal-5'-phosphate. Pyridoxylation has been shown to favorably alter the reversible oxygen binding capacity, i.e. increase the $P_{50}$ of certain mammalian hemoglobins, e.g. human hemoglobin.

"Stable" or "stability" refer to the state or characteristic of hemoglobin solutions that are resistant to degradation and have a longer shelf life than non-stable solution. For example, hemoglobin solution that have been stabilized according to the invention will, compared to solutions that have not been prepared according to the invention, have less or slower tetramer elaboration during storage of the solution. The stability of a hemoglobin solution is dependent on several other parameters that are independent of tetramer elaboration, including, for example, how quickly deoxyhemoglobin is converted to oxyhemoglobin or methemoglobin. This parameter may be controlled by, among other ways, preventing oxygen from entering the packaged solution during storage. Stabilized hemoglobin solutions may still degrade, but do so at a slower rate than non-stabilized solutions.

The invention provides a polymerized, hemoglobin solution essentially free of tetrameric (native or intramolecularly crosslinked) hemoglobin, stromal and various other contaminants. The solution is physiologically acceptable as well as therapeutically and clinically useful. The product has reversible oxygen binding capacity which is necessary for oxygen transport properties. The product demonstrates good oxygen loading and unloading characteristics in usage, which correlates to having an oxygen-hemoglobin dissociation curve ($P_{50}$) similar to whole blood. The product binds oxygen with high affinity in the capillaries through the lungs and then adequately releases oxygen to the tissues in the body. The product also does not require compatibility studies with the recipient.

In one aspect, the product may also have a half-life when administered to humans of about at least 15 hours. In another aspect, the half life is greater than about 24 hours. The hemoglobin product can be used to replenish essentially all of a human patient's blood volume without causing vasoconstriction, renal toxicity, hemoglobinuria or other problems associated with intravenous administration of synthetic or semi-synthetic oxygen carriers and blood substitutes.

The half-life of the resulting product of the invention is determined in vivo in mammals, e.g., humans. Typically, a blood sample is removed from the mammal a period of time after the mammal has been infused with the product. The amount of the product is then determined by centrifuging the blood sample, expressing the plasma portion, determining plasma hemoglobin levels spectrophotometrically, and then correlating the amount of product remaining in the mammal to the half-life of the product.

The method of the invention yields a stabilized polymerized hemoglobin solution with an enhanced shelf life. Generally, tetramer elaborates as the polymerized hemoglobin solution ages. Elaborated tetramer can be removed from the aged hemoglobin solution by the process of the invention. Aged hemoglobin solutions that have been processed to remove tetramer exhibit slower tetramer elaboration upon further storage as compared to newly processed (non-aged) hemoglobin solutions. Thus, hemoglobin solutions processed according to the invention exhibit a greater stability with respect to tetramer elaboration than newly processed solutions.

Figure 2:
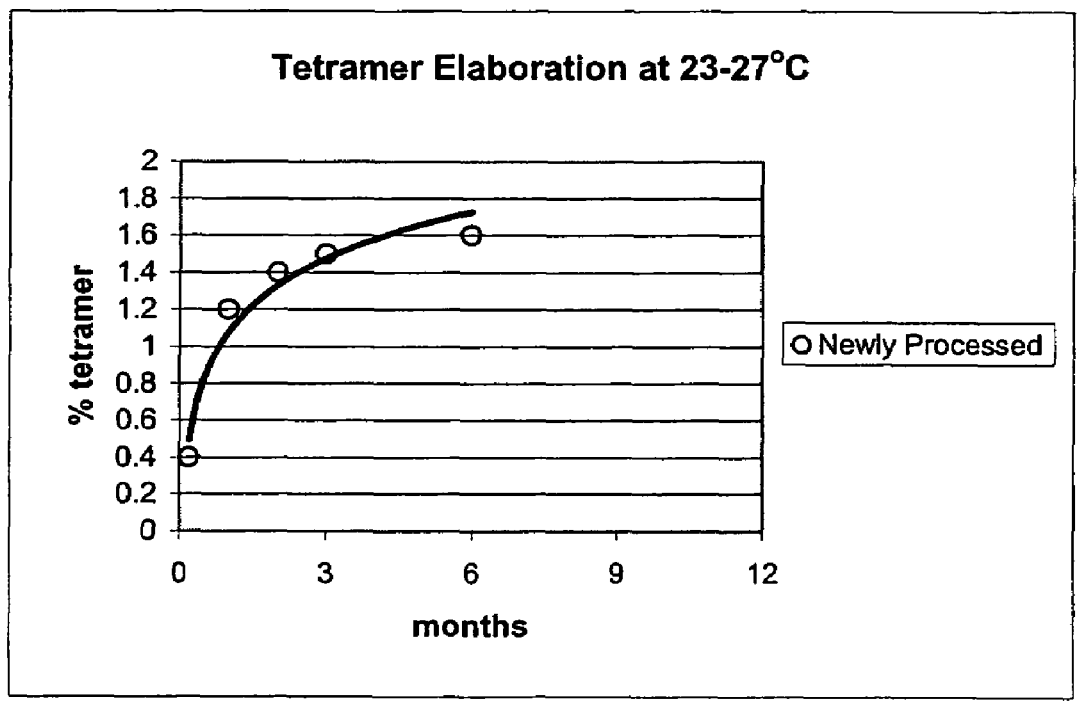
FIG. 2 shows the amount of tetramer elaboration in hemoglobin solutions stored at 23-27° C.

Generally, it has been found that physiologically and clinically useful hemoglobin solutions contain less than 1.0% tetramer. Accordingly, since tetramer elaborates over time during storage, to allow a reasonable shelf life for the hemoglobin solution, it is desirable that newly processed hemoglobin solutions contain less that about 0.3% tetramer, with the expectation that tetramer in solution will elaborate, but the solution will remain physiologically useful until tetramer reaches 1.0%. FIG. 1 shows the typical amount of tetramer elaboration of a hemoglobin solution stored at 2-8° C. In a solution with beginning tetramer levels of about 0.5%, tetramer levels rise to greater than 1.0% after about 18 months. FIG. 2 shows the typical amount of tetramer elaboration for a hemoglobin solution stored at 23-27° C. In a solution with a beginning tetramer level of about 0.5%, tetramer levels rise to above 1.0% in about 3-4 weeks. Thus, storage of hemoglobin solutions at increased temperatures increases the rate of tetramer elaboration. Aging of tetramer solutions can be accomplished merely be allowing the hemoglobin solution to stand for extended periods of time. Higher temperatures age the hemoglobin solutions faster than lower temperatures.

Figure 3:
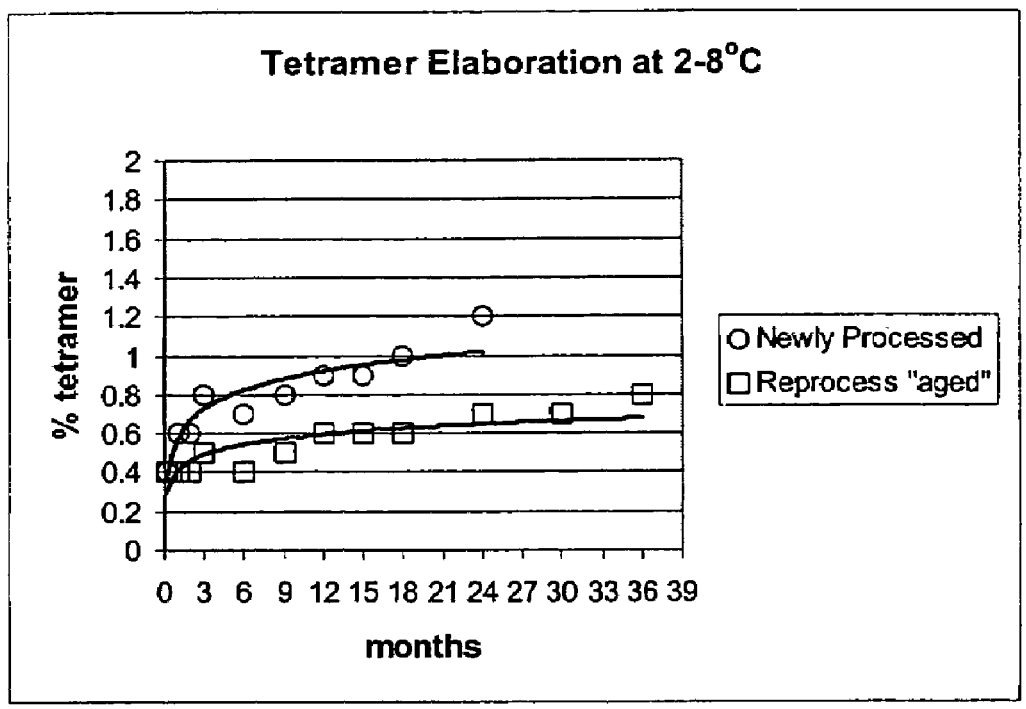
FIG. 3 shows a comparison of tetramer elaboration between newly processed hemoglobin solutions and reprocessed aged hemoglobin solutions stored at 2-8° C.
Figure 4:
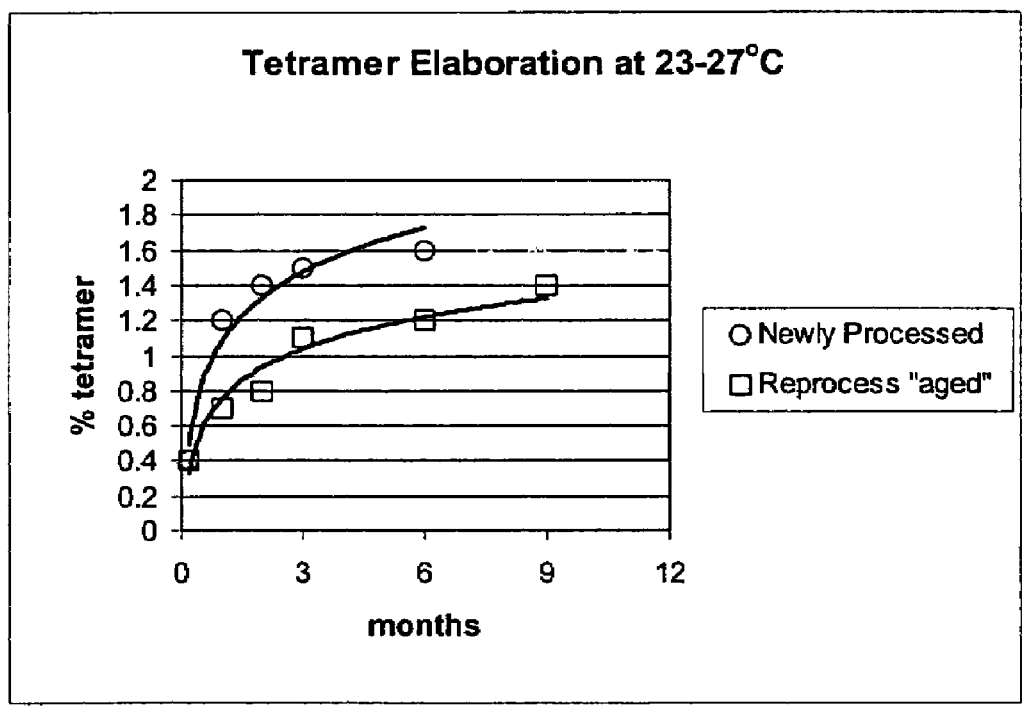
FIG. 4 shows a comparison of tetramer elaboration between newly processed hemoglobin solutions and reprocessed aged hemoglobin solutions stored at 23-27° C.

FIG. 3 shows a comparison of the tetramer elaboration between a newly processed hemoglobin solution and an "aged" hemoglobin solution processed according to the invention ("reprocessed"). Both solutions were stored at 2-8° C. After 24 months, tetramer increased about 0.8% in the new hemoglobin solutions while, in the reprocessed solution, tetramer increased only about 0.3%. Over 36 months the tetramer in the reprocessed solution increased about 0.4%. Likewise, FIG. 4. shows that tetramer elaborates faster in newly processed solutions as compared to reprocessed solutions when stored at 23-27°.

In one aspect, the method of the invention involves pre-elaborating the hemoglobin solution to enhances the stability of a solution by heating the solution to accelerate tetramer elaboration. The elaborated tetramer can be removed from the solution to provide a solution that is more stable with respect to tetramer elaboration than polymerized solutions that have not been heat treated to accelerate tetramer elaboration. Once elaborated tetramer has been removed from the hemoglobin solution, further tetramer elaboration is slowed or decreased.

Heat treatment may occur either before or after purification of the solution. If the solution is heat treated during processing, such heat treatment should follow polymerization of the solution. The solution can then be purified to remove substantially all the tetramer. If heat treated after purification, the solution must be re-purified to remove the elaborated tetramer.

Heat treating may be accomplished by subjecting the polymerized hemoglobin solution to about 45-55° C. for about 20-30 hours. It is expected that other processing temperatures and time will suffice in order to elaborate tetramer since it has been shown that tetramer elaboration is a function of, among other things, time and temperature.

The process of the invention provides a further advantage in that it can render the final product substantially free of microbial and viral antigens and pathogens. Such microbial and viral antigens and pathogens are reduced to non-detectable levels, i.e., the product is sterile as determined by the analysis set forth in the United States Pharmacopoeia, XXIII Chapter 71. Examples of such antigens and pathogens include, for example, bacterial, rickettsial, fungal, protozoan, viral and other organisms. Most importantly, the process provides a biological product free of viruses that cause hepatitis and acquired immune deficiency syndrome (AIDS).

Heat treatment of the hemoglobin solution results in the substantial inactivation of viruses. Viral inactivation heat treatment can be a separate step of heat treatment or may be combined with the heat treatment to remove tetramer. Generally, for the purposes of production operator safety, it is preferred that viral reduction heat treatment be conducted after the hemoglobin has been removed from red blood cells. However, it is expected that heat treatment of the solution following polymerization will also accomplish the desired viral inactivation. If a pre-polymerization viral reduction heat treatment step has been eliminated, temperature of the post-polymerization heat treatment to elaborate tetramer can be increased to about 60-62° C., or other suitable temperature, to ensure viral inactivation. Thus, one heat treating step following polymerization will, in certain aspects, accomplish both viral reduction and tetramer elaboration.

The biological product of this invention, when infused in amounts of up to at least about 10.0 L, does not cause vasoconstriction, renal toxicity, hemoglobinuria and other problems implicated with intravenous administration of known hemoglobin solutions containing physiologically undesirable amounts of tetrameric hemoglobin. Intravenous administration of the product produced by the process described herein results in no appreciable decrease in urine production, no appreciable decrease in glomerular filtration rate, no appreciable extravasation into the peritoneal cavity and no appreciable change in the color of urine produced.

Therefore, the process of the invention provides an acellular red blood cell substitute useful in the treatment of trauma, myocardial infarction, stroke, acute anemia and oxygen deficiency disorders such as hypoxemia, hypoxia or end stage hypoxia due to impairment or failure of the lung to fully oxygenate blood. The product also is useful in the treatment of any disease or medical condition requiring a resuscitative fluid (e.g., trauma, specifically hemorrhagic shock), intravascular volume expander or exchange transfusion. In addition to medical treatment, the product can be useful in preserving organs for transplants.

In one aspect, the starting material in the process of the invention is whole human blood or packed red blood cells. Generally, it is desirable, but not critical, to use source red blood cells that have been in storage for no more than 2 weeks past the expiration date indicated on the blood storage bag. The use of human whole blood outdated by more than 2 weeks provides additional difficulty in extracting the hemoglobin and removing cellular remnants such as stromal proteins and contaminants. In addition, the processes described herein are applicable to all hemoglobins with minor modifications within the skill of the art.

If human blood is used as a staring material, during red cell aspiration and filtration, the red blood cells (RBC) are aseptically extracted from donor bags without introducing air into the blood and passed across a series of filters to result in a RBC suspension having reduced amounts of leukocytes and platelets. The resulting suspension is then subjected to cell washing/lysing.

The suspension is washed under carbon monoxide atmosphere with an about 1% NaCl solution to remove residual plasma proteins. The washed RBC are then treated with water for injection ("WFI") to lyse the cells and the resulting mixture is clarified using a cross flow filtration unit. Other methods of lysing red blood cells known to those of skill in the art may be used including, for example, mechanically or sonically lysing the cells. The clarified product may then be heat-treated for viral inactivation and to precipitate additional stromal material which is removed by filtration. The product of this procedure is a stroma-free hemoglobin (SFH) solution with a THb of about 3% (w/v).

Following clarification, the solution containing carboxyhemoglobin is preferably concentrated and degassed to yield a stroma free hemoglobin solution containing deoxyhemoglobin. Degassification involves first saturating the carboxyhemoglobin solution with oxygen for about 16 hours to yield a solution of oxygenated hemoglobin and about 7% by weight, based on the total weight of hemoglobin, of carboxyhemoglobin. Subsequently, the oxygen is driven off with nitrogen, argon or helium to form a solution containing free hemoglobin, i.e., uncomplexed hemoglobin, and about 7% by weight, based on the total weight of hemoglobin, of oxyhemoglobin. The resulting degassed solution is filtered and transferred into a vessel for chemical modification.

Subsequent to degassification, the stroma-free hemoglobin solution comprising human hemoglobin should be pyridoxylated using pyridoxal-5'-phosphate (P5P) at a molar ratio of pyridoxal-5'-phosphate to hemoglobin of about 1:1 to 3:1. Alternatively, the stroma-free hemoglobin may be pyridoxylated using 2-Nor-2 formyl pyridoxal-5'-phosphate. A reducing agent such as sodium cyanoborohydride or preferably sodium borohydride is added to the pyridoxylation mixture. Excess reagents and salts are removed by dialysis against pyrogen free water or, preferably, diafiltration with WFI. Hemoglobin from sources other than human blood may not need pyridoxylation. Those skilled in the art of hemoglobin solutions readily understand when pyridoxylation is required.

The stroma-free, hemoglobin solution is polymerized using any method known to those skilled in the art of hemoglobin solutions. Preferably, an aqueous glutaraldehyde is used as a polymerizing agent. The duration of polymerization and the amount of glutaraldehyde added is dependent on volume of the hemoglobin solution, the desired yield of polymers and the desired molecular weight distribution. In general, longer polymerization times increase the yield and the molecular weight distribution of the polymers. A yield of approximately 75% by weight of polymers, based on the total weight of hemoglobin, is obtained in about 16-18 hours. The preferred end point of the polymerization is defined as that point where the solution contains about 75% by weight of polymers, based on the total hemoglobin weight, as monitored by size-exclusion HPLC. Alternatively, the endpoint is defined as the point at which the solution contains about 65% of polymers based on the total weight of hemoglobin, i.e., about 2.5 hours.

Following polymerization, the reaction should be quenched with the appropriate agent. In one aspect, the polymerization reaction is quenched by the addition of aqueous glycine. The glycine should be added as quickly as possible. The cross-links are then stabilized by adding, again as quickly as possible, a solution of aqueous sodium borohydride. This polymerized solution is subsequently concentrated and then diafiltered. Water is finally added to the solution until the solution contains about 4% by weight hemoglobin.

Figure 5:
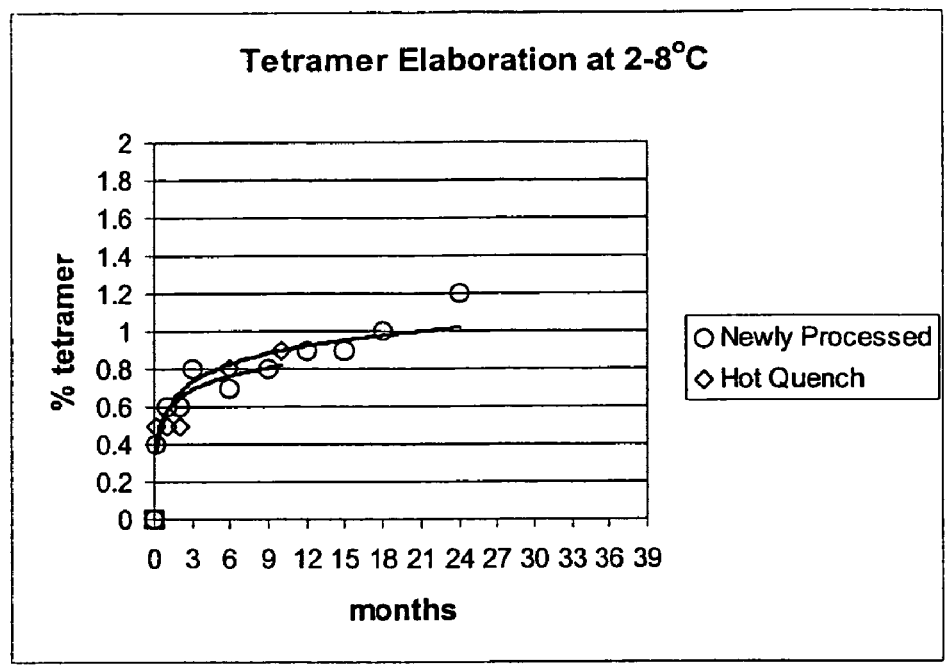
FIG. 5 shows a comparison of tetramer elaboration between newly processed hemoglobin solutions and hot quenched solutions stored at 2-8° C.
Figure 6:
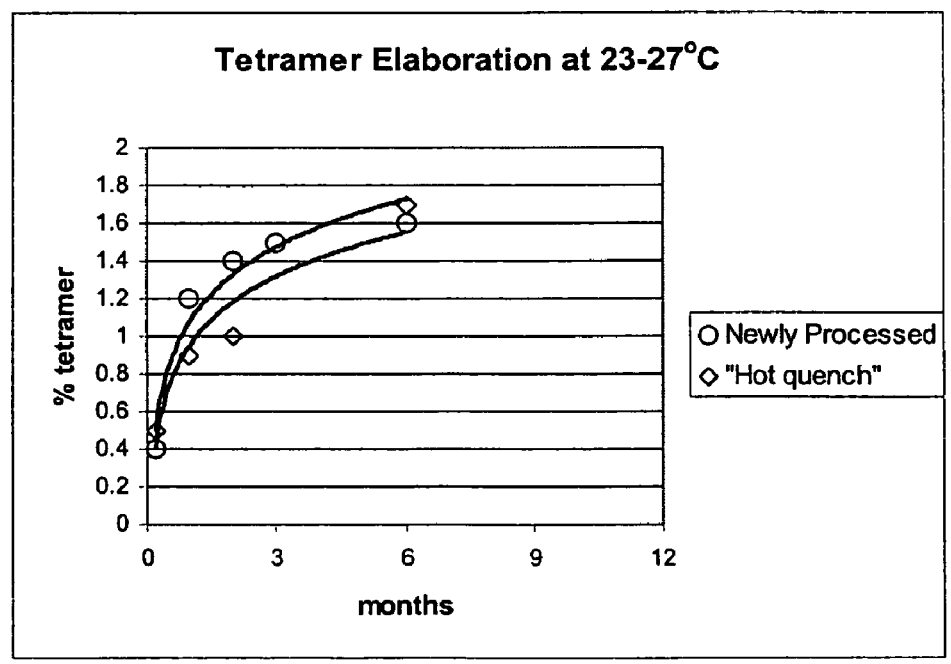
FIG. 6 shows a comparison of tetramer elaboration between newly processed hemoglobin solutions and hot quenched solutions stored at 23-27° C.

In another aspect, the solution may be "hot quenched" by heating the solution to 40-50° C. for at least three hours concurrent with the addition of glycine to drive the quench reaction to completion. FIG. 5 shows a comparison of the tetramer elaboration between a newly processed hemoglobin solution and a hemoglobin solution subject to a hot quench for three hours. Both solutions were stored at 2-8° C. After 10 months, tetramer increased between 0.4-0.5% in the new hemoglobin solution while, in the hot quenched solution, tetramer increased only about 0.4%. FIG. 6 shows the differences in tetramer elaboration between newly processed solutions and hot quenched solutions when stored at 23-27° C. It is expected stability of the solution would be enhanced by subjecting to the solution to a longer hot quench, for example, up to twenty-four hours. Higher temperatures, up to about 65° C., may also be employed.

Figure 9:
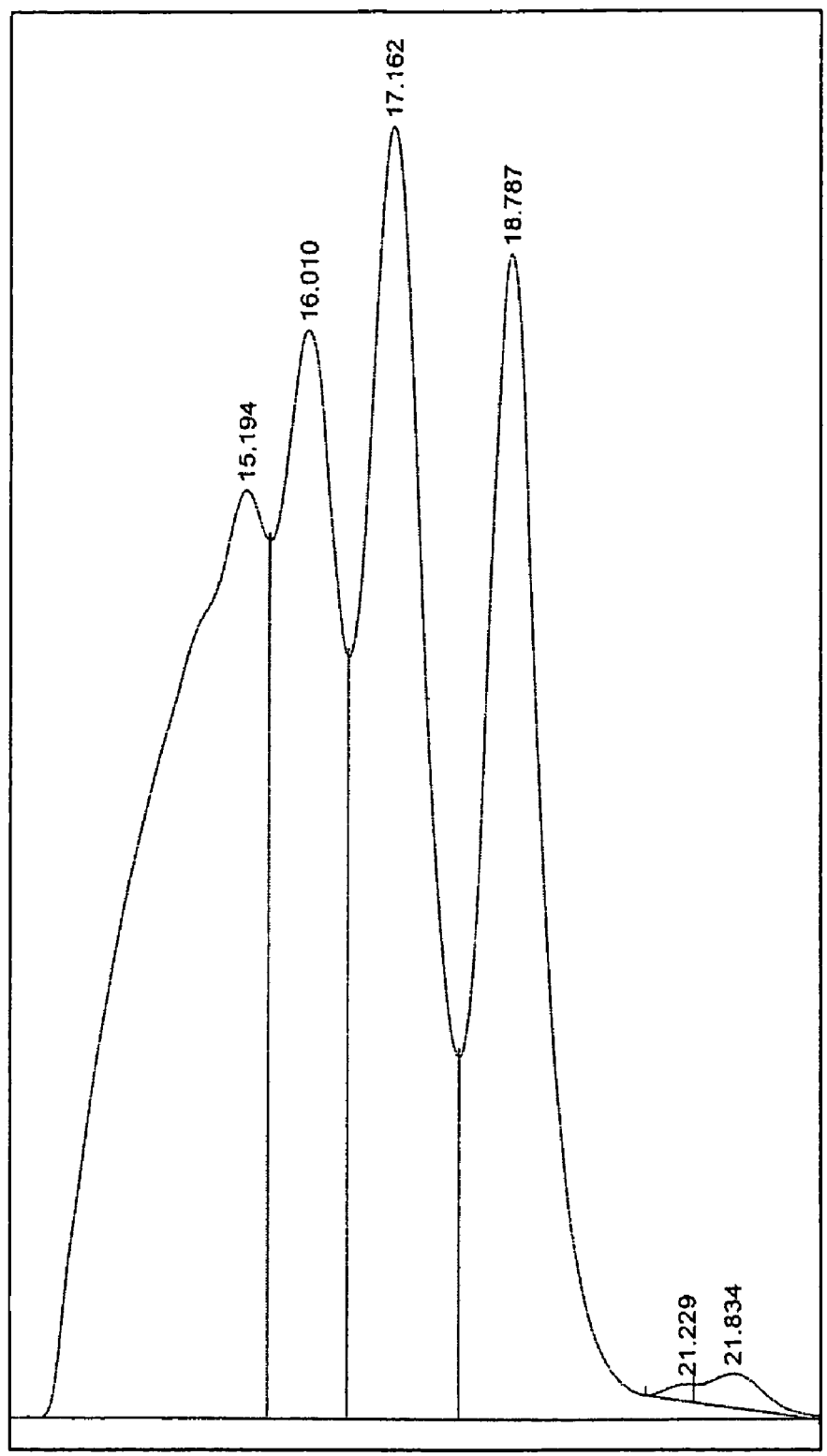
FIG. 9 is an HPLC tracing of a purified, polymerized hemoglobin solution. Polymerized hemoglobin is indicated by the peaks at RT 15.19, 16.01, 17.16 and 18.79. Tetramer is indicated by peaks at RT 21.22 and 21.83.

Polymerization according to the invention results in a high yield of polymers having a narrow molecular weight range as shown in FIG. 9 and the Examples below.

In another aspect, the post-quench polymerized solution may be pre-elaborated by heat treatment to elaborate tetramer. The heat treatment may be postponed until any point after purification, but the solution would require repurification. Heat treatment may be accomplished by heating the solution to above about 45° C. for at least about 24 hours. If viral inactivation is desired at this point, the solution may be heated to above about 60° C. An antioxidant such as ascorbic acid may be added to prevent formation of methemoglobin during the heat treating process.

Figure 7:
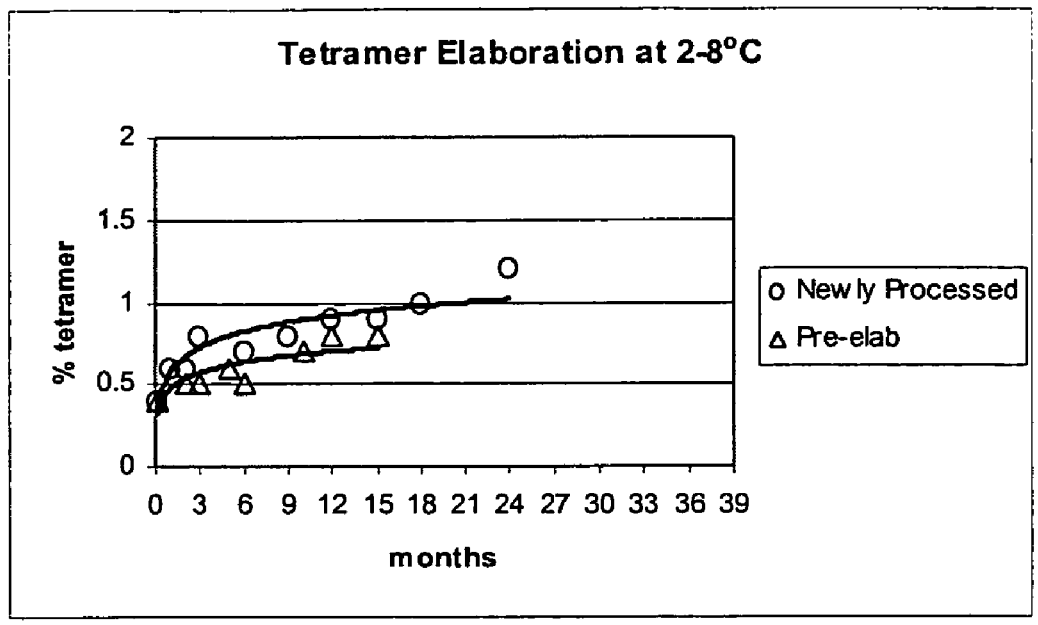
FIG. 7 shows a comparison of tetramer elaboration between newly processed hemoglobin solutions and pre-elaborated solutions stored at 2-8° C.
Figure 8:
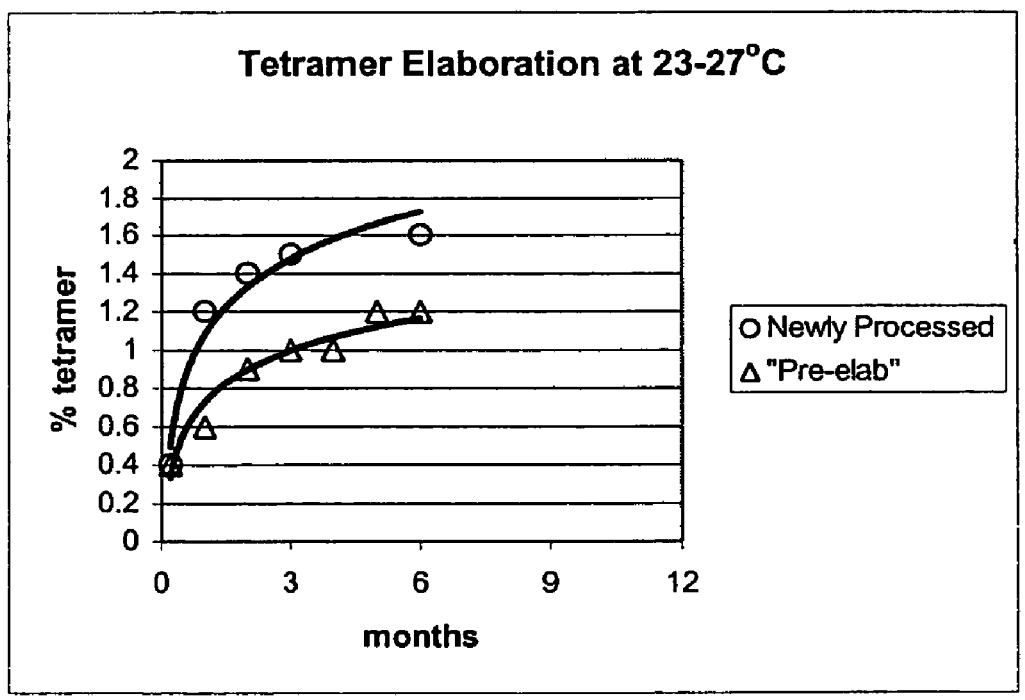
FIG. 8 shows a comparison of tetramer elaboration between newly processed hemoglobin solutions and pre-elaborated solutions stored at 23-27° C.

FIG. 7 shows a comparison of the tetramer elaboration between a newly processed hemoglobin solution and a pre-elaborated hemoglobin solution processed according to the invention. Both solutions were stored at 2-8° C. After 15 months, tetramer increased about 0.5% in the new hemoglobin solutions while, in the pre-elaborated solution, tetramer increased only about 0.4%. Likewise, FIG. 8 shows that tetramer elaborates faster in newly processed solutions as compared to pre-elaborated solutions when stored at 23-27° C.

The polymerized, pyridoxylated hemoglobin solution is then purified. In one aspect, purification is accomplished under an atmosphere of oxygen to oxygenate the solution utilizing column chromatography, filtration, e.g., membrane filtration, or both, to remove residual unpolymerized (tetrameric) hemoglobin from the solution. The purified polymerized hemoglobin solution is then concentrated to about 6% using an ultrafiltration apparatus in preparation for gas exchange.

The concentrated solution is then deoxygenated with nitrogen. The deoxygenation takes place at about 10-12° C. until the amount of oxyhemoglobin in the solution is less than about 16% by weight of the total hemoglobin.

The resulting deoxygenated, purified, and polymerized hemoglobin solution is then concentrated by ultrafiltration under a nitrogen atmosphere in a cooled vessel. The pH is adjusted to about 8.8-9.0, and the amounts of electrolytes may be adjusted as necessary to levels representing that of normal plasma. In addition, conventional antioxidants such as glutathione, ascorbate or glucose may be optionally added. After the solution is concentrated to the desired level, preferably about 10% by weight total hemoglobin, the solution is sterilized by filtration and transferred via a sterile transfer apparatus into suitable pharmaceutically acceptable containers.

If the hemoglobin solution was not previously heat treated to facilitate tetramer elaboration, the solution may be heat treated and repurified to remove elaborated tetramer. If antioxidants and formulation chemicals have been added, these may be removed by diafiltration prior to heat treatment and purification.

In addition, as an alternative to heat treatment, tetramer elaboration of the finished hemoglobin solution may be accomplished by allowing the solution to age at an appropriate temperature. The solution can then be repurified to remove the elaborated tetramer. Generally, it is expected that the solution should age until tetramer levels exceed about 1-3%, with higher tetramer levels giving increased stability benefits after the solution is purified to remove tetramer. However, it is expected that the advantages of the invention will be accomplished if the solution is aged for any period of time, so long as the elaborated tetramer is removed after aging of the solution.

The characteristics of the resulting hemoglobin solution are shown in FIG. 9 and are as follows:

| | |
|---|---|
| Total Hemoglobin (g/dl) | 9.5-10.5 |
| Methemoglobin (% of total Hb) | <8.0 |
| Carboxyhemoglobin (% of total Hb) | <5.0 |
| $P_{50}$ (torr) | 26-32 |
| Osmolality (mmol/Kg) | 280-360 |
| Sodium (mmol/L) | 135-155 |
| Potassium (mmol/L) | 3.5-4.5 |
| Chloride (mmol/L) | 85-110 |
| Free Iron (ppm) | <2.0 |
| Molecular Wt. Dist. - 128 Kd peak (%) | 9-23 |
| Molecular Wt. Dist. - 192 Kd peak (%) | 16-18 |
| Molecular Wt. Dist. - 256 Kd peak (%) | 49-74 |
| Tetramer (64K)(%) | ≤1.0 |
| Endotoxin (EU/mL) | <0.03 |
| Phospholipids ng/Hb | <50 |
| Glycolipids (ng/Hb) | <2 |

EXAMPLES

The following examples demonstrate certain aspects of the invention. However, it is to be understood that these examples are for illustrative purposes only and do not purport to be wholly definitive as to conditions and scope of this invention. All temperatures are expressed in degrees Celsius unless otherwise specified. It also should be appreciated that when typical reaction conditions (e.g., temperature, reaction times) have been given, the conditions which are both above and below these specific ranges can also be used, though generally less conveniently.

Unless noted to the contrary, all vessels and tanks used in the inventive process are made of 316-L Stainless Steel, preferably a pharmaceutical grade of such stainless steel that has been highly polished and therefore easily and rapidly cleaned. The various connecting pipes and tubes are made of the same stainless steel or of a pharmaceutical grade Teflon or silicone tubing. The filters and membranes used in the process may be purchased from Millipore Inc., Pall-Filtron, or Cuno Inc.

Analytical Size Exclusion Chromatography HPLC according to the invention is carried out according to the following procedure. The sample is diluted to 0.2 g/dl with 0.1 M sodium phosphate buffer at about pH 6.9, filtered through a 0.2µ filter and injected into an HPLC system consisting of the following components (in order of system flow):

1. Agilent Technologies 1100 Isocratic Pump
    mobile phase is 0.1 M sodium phosphate at about pH 6.9
    flow rate is 0.5 mL/minute
2. 45 cm PEEK or titanium tubing, 0.010 in. I.D.
3. Agilent 1100 Autosampler
4. 18 cm PEEK or titanium tubing, 0.010 in. I.D.
5. 0.5µ precolumn filter frit
6. 9 cm PEEK or titanium tubing, 0.010 in. I.D.
7. Toso TSK G3000SWXL 40×60 mm guard column
8. 24 cm PEEK or titanium tubing, 0.010 in. I.D.
9. Toso TSK G3000SWXL 300×7.8 mm Analytical column
10. 23 cm PEEK or titanium tubing, 0.010 in. I.D.
11. Agilent 100 variable wavelength detector.

| | |
|---|---|
| wavelength: | 280 nm |
| flow cell: | 14 µL vol., 10 mm pathlength |
| range: | 2 AUFS |
| time constant: | 10 seconds |

The peak absorbance at 280 nm is recorded by an Agilent Chemstation, which integrates the individual peak areas and calculates the total Hemoglobin area for each polymeric species.

Example 1

Cell Aspiration and Filtration

Figure 11:
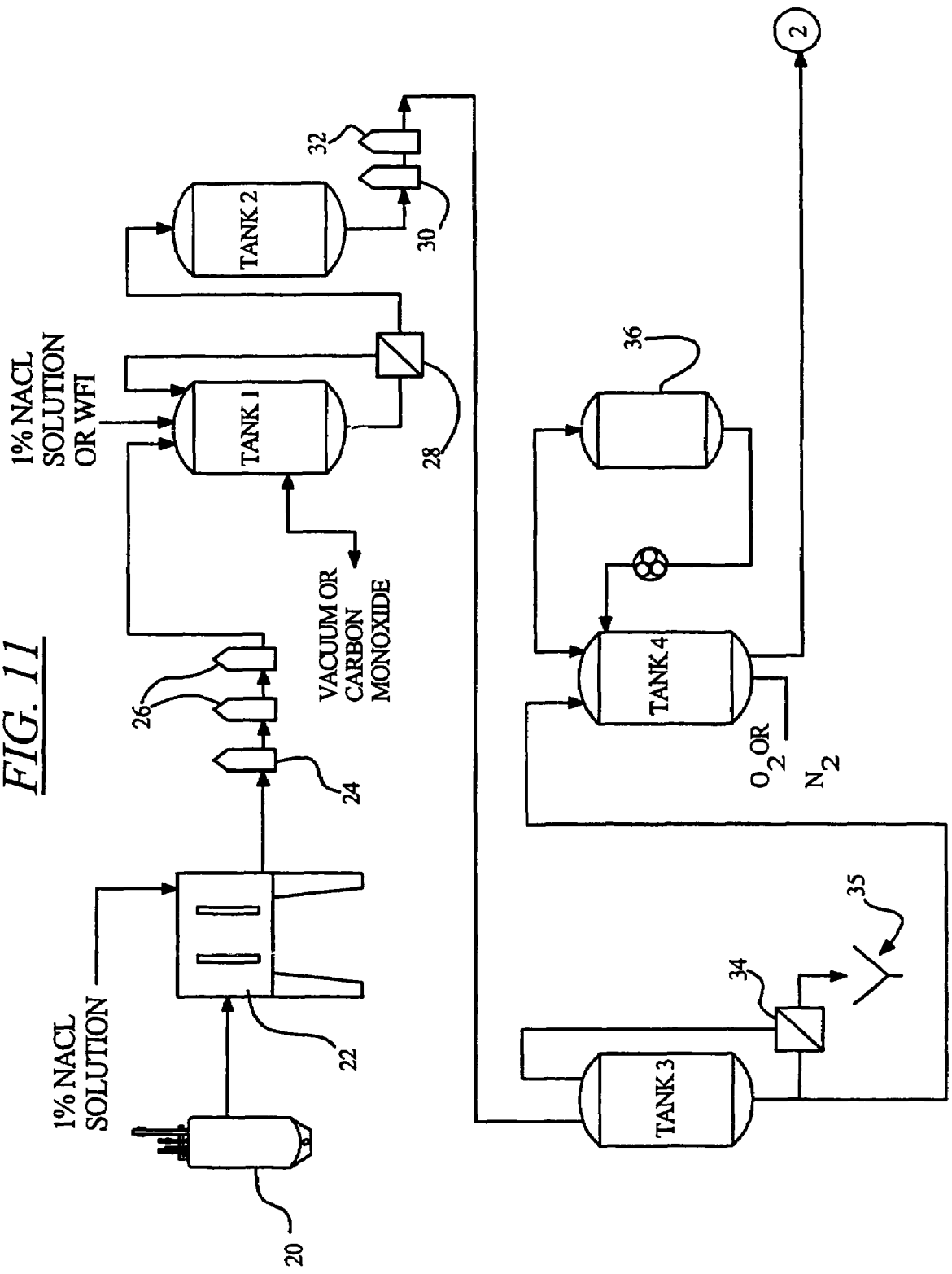
FIG. 11 is a schematic diagram depicting the portion of the process and equipment used to produce a deoxygenated hemoglobin solution prepared for pyridoxylation and polymerization.

Referring now to FIG. 11, donor bags 20 of outdated blood (whole blood or packed red blood cells) are situated in a suitable aseptic aspiration apparatus 22. A needle in the aspiration apparatus punctures the donor bag, introduces about 150 ml of a 1% (w/v) aqueous sodium chloride solution and aspirates the outdated blood from the donor bag under reduced pressure or vacuum. The aspirated blood is passed through leukocyte adsorption depth filter 24 or alternatively through two 5µ depth filters in series 26. As the blood passes through the filters, leukocytes are removed from the blood. Typically, about 225 units of outdated whole blood are aspirated, filtered and subsequently transferred to Tank 1 as shown in FIG. 11. The filters are then rinsed with about 75 liters of a 1% (w/v) aqueous sodium chloride solution.

Example 2

Cell Wash and Lysis

Prior to the introduction of the blood into Tank 1, Tank 1 is charged with about 40-50 L of a 1% aqueous sodium chloride solution. After all 225 units of outdated whole blood have been aspirated, filtered and transferred, and the filters have been rinsed, the tank contains about 365-395 liters of a 4% total hemoglobin solution. During the aspiration and filtering steps, Tank 1 is maintained at a reduced pressure, i.e., a vacuum of 20-28 inches Hg. Once all the outdated blood has been transferred to Tank 1, the vacuum is switched off and carbon monoxide is introduced into the tank so that the tank contains an atmosphere of carbon monoxide.

Tank 1 is coupled to a 0.65µ tangential flow filter 28 as shown in FIG. 11. The initial charge of 365-395 liters of 4% total hemoglobin solution is concentrated to approximately 215-225 L of a 7% total hemoglobin solution by microfiltration through the tangential flow filter. The pH of the hemoglobin solution at this point is about 6 to 6.5. Subsequent to concentrating to 7% total hemoglobin, the solution is washed by adding a 1% (w/v) sodium chloride solution, diafiltering and removing the filtrate at the same rate sodium chloride solution is added. The 215-225 L of hemoglobin solution is typically washed with about 8 volumes of the 1% sodium chloride solution (about 1,800 L). Subsequent to washing, the solution is concentrated to about 90-95 L, i.e., about 16% total hemoglobin, and water for injection ("WFI") is added to bring the volume of the solution up to about 220 L. With the addition of the WFI, the cells swell and rupture releasing hemoglobin into solution. The concentration of the resulting hemoglobin solution is about 7% total hemoglobin (THb).

The resulting solution is clarified while still in Tank 1. The solution is first concentrated to about 90 L and the filtrate is transferred to Tank 2. As the solution is pumped across the filter, red blood cells, stroma contaminants and cell wall material is retained and removed by the filter. The remaining 90 L of solution in Tank 1 is washed (diafiltered) with about 280 L of WFI and the wash is added to Tank 2. The material remaining in Tank 1 is then concentrated to about 20 L and the filtrate added to Tank 2. The volume resulting in Tank 2 is about 405-415 L of a 3.3% total hemoglobin solution.

Example 3

Optional Heat Treatment For Viral Reduction and Stromal Precipitation

The resulting solution of stroma-free hemoglobin is then heat treated in Tank 2 at a temperature of about 60-62° C. over a period of about 10 hours. During this time, the solution is moderately agitated. As the solution is heated and passes a temperature of about 55° C., a precipitate forms.

Example 4

Clarification and Viral Reduction

The resulting 3.3% THb stroma-free, heat treated hemoglobin solution is then filtered through a 0.2µ prefilter 30 followed by a 0.1µ prefilter 32 and then pumped through a 100 kD viral reduction ultrafilter (not shown) into Tank 3.

Example 5

Ultrafiltration/Concentration

The filtered hemoglobin solution is then concentrated to 85-105 L (about 14% THb) and subsequently washed and diafiltered with about 4 volumes of WFI (350 L). The concentration and diafiltration is accomplished using a 10 kD molecular weight ultrafilter 34. Drain 35 associated with ultrafilter 34 collects filtrate. At this point, the 14% total hemoglobin solution contains less than about 50 ng of phospholipid per gram of hemoglobin, less than about 2 ng of glycolipid per gram of hemoglobin, less than about 1% methemoglobin, less than about 0.03 units of endotoxin per milliliter at a pH of about 6 to 6.5. The hemoglobin in the solution is carboxyhemoglobin.

Example 6

Degassification

The resulting carboxyhemoglobin solution is then transferred to a 175 L vessel (Tank 4) where the carboxyhemoglobin is first oxygenated and then deoxygenated. Tank 4 is fitted with a gas sparge ring coupled to oxygen and nitrogen gas lines, a feed from the tank bottom to a metered spray apparatus positioned at the top of Tank 4, and a foam overflow collector connected to foam can 36 such that foam generated in Tank 4 is fed into foam can 36 where the foam condenses into liquid and is fed back into Tank 4. As an alternative to the foam can 36, Tank 4 can be fitted with a mechanical foam breaker. Tank 4 further includes a center mounted, gas dispersion agitator. Foam can 36 includes a gas vent for removal of gas. The solution in Tank 4 is a 13% total hemoglobin solution.

During a first oxygenation step, oxygen is sparged through the solution at a rate sufficient to have uniform dispersion of gas in the vessel. The vessel is sparged at a rate of about 66 L/min. with gas. Oxygenation of the carboxyhemoglobin is conducted for a period of about 18 hours such that the resulting solution contains less than 5% carboxyhemoglobin based on the weight of total hemoglobin. Oxygenation is conducted at a temperature of about 10° C. The foam generated in Tank 4 is collected in Foam Can 36 and after settling, the resulting solution is transferred back into Tank 4.

After oxygenation, the solution is sparged with a similar flow of nitrogen for about 3-3.5 hours or until less than 10% oxyhemoglobin based on the weight of total hemoglobin remains in the solution. The nitrogen sparge is conducted at a temperature of about 10° C. and a pH of about 6.95-7.10. Alternatively, carboxyhemoglobin could be converted to deoxyhemoglobin using a membrane exchanger. It is noted that there is substantially no denaturing of the hemoglobin as would normally be expected from the foaming step.

Example 7

Chemical Modification

Figure 12:
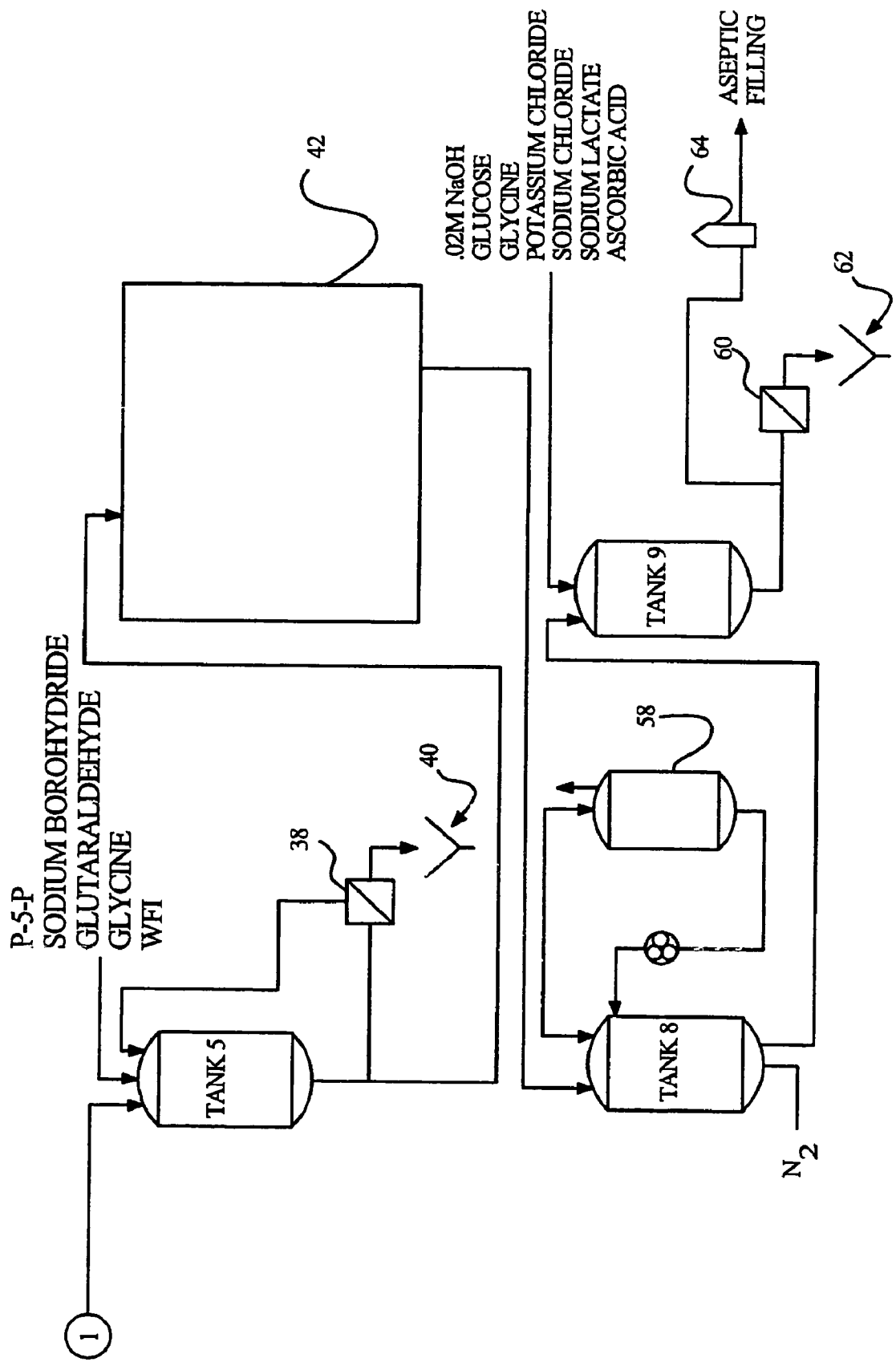
FIG. 12 is a schematic diagram depicting the portion of the process and apparatus to produce, beginning with pyridoxylation and polymerization, a deoxygenated, purified, pyridoxylated, polymerized hemoglobin product, and the portion of the process and apparatus for formulating the final hemoglobin product having physiological levels of electrolytes.

Referring now to FIG. 12, the deoxyhemoglobin solution is transferred to Tank 5 for chemical modification. To Tank 5 containing the deoxyhemoglobin solution at about 4° C. is then added an aqueous solution of pyridoxyl-5-phosphate (P5P) (93.75 g/L) at a 1:1 to 3:1 P5P to hemoglobin molar ratio. A 2:1 molar ratio of P5P to hemoglobin is preferred. The pyridoxylation is conducted at a temperature of about 4° C. The P5P solution is typically added over about 1 minute and mixed for approximately 15 minutes, after which a sodium borohydride/sodium hydroxide solution is added to the hemoglobin solution at a molar ratio of sodium borohydride to hemoglobin of about 20:1. A suitable aqueous sodium borohydride/sodium hydroxide solution contains 0.8 g of sodium hydroxide per 2 liters and 90.8 g of sodium borohydride per 2 liters. The borohydride solution is added as rapidly as possible over a period of about 1 minute and then stirred for one hour.

Example 8

Reactant Removal

The resulting 150 L solution of pyridoxylated hemoglobin is subsequently diafiltered using 10K Dalton ultrafilter 38 to remove excess reactants with 4 volumes (600 L) of WFI. Drain 40 associated with ultrafilter 38 collects the filtrate from filter 38.

Example 9

Polymerization

To Tank 5 containing the pyridoxylated hemoglobin is added sufficient WFI to prepare a 4.5% total hemoglobin solution (about 265 L of hemoglobin solution). A glutaraldehyde solution is added to the pyridoxylated hemoglobin solution at a molar ratio of glutaraldehyde to hemoglobin of about 24:1. The glutaraldehyde solution is typically added over a period of about 2.5 hours by a metering pump to the hemoglobin solution. The polymerization reaction is allowed to proceed for about 18 hours. The target molecular weight distribution is about 75% polymer and 25% tetramer. The target polymers have molecular weights of less than about 600,000 with a predominant fraction of the molecular weights residing in the 100,000-350,000 range.

When the polymerization reaction reaches the target molecular weight distribution (after about 18 hours), aqueous glycine (about 166 g/L) is added (as a quench) to the hemoglobin solution at a 140:1 molar ratio of glycine to hemoglobin. At thus point, the solution may be heated to 40-50° C. for at least three hours to drive the quench reaction to completion ("hot quench").

Figure 10:
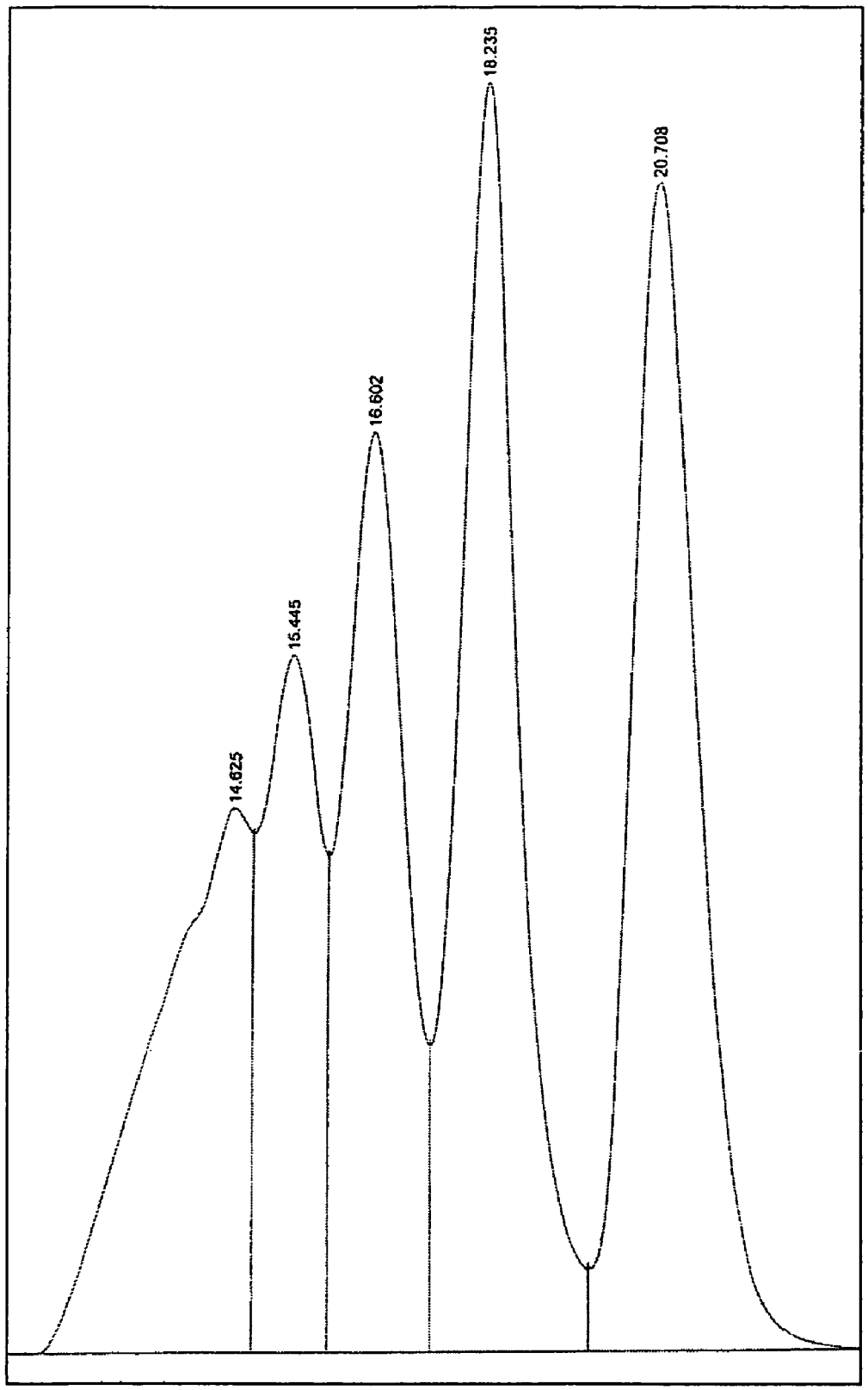
FIG. 10 is an HPLC tracing of a polymerized hemoglobin solution after glycine treatment but prior to purification. Polymerized hemoglobin is indicated by peaks at retention times (RT) 14.62, 15.44, 16.60, and 18.24. Tetramer is indicated by the peak at RT 20.71. Polymer is about 75% of this material.

FIG. 10 shows an HPLC tracing of the resulting polymerized, glycine-quenched hemoglobin product. The resulting solution is then mixed for about 10 minutes after which a sodium borohydride sodium/hydroxide solution (having the concentration identified above) is added to the hemoglobin solution at a 28:1 molar ratio of sodium borohydride to hemoglobin. This resulting mixture is stirred for about 1 hour. The solution is then concentrated to about 150 L (ultrafilter 38) and washed with 4 volumes (600 L) of WFI. An additional aliquot of sodium borohydride at the same molar ratio as indicated above is added to the concentrated solution and again mixed for 1 hour. The resulting solution is washed with 4 volumes of WFI (600 L).

Example 10

Optional Heat Treatment for Tetramer Elaboration

At this point, the solution may be heat treated to elaborate tetramer. The solution may be subject to heating at 45-55° C. for about 20-30 hours. If the viral reduction is desired during this step, the temperature may be increased to above 60° C. To heat the solution, a heating medium, such as a propylene glycol solution at about 80° C., is circulated through the tank jacket while vigorously agitating the Hb solution. After heating, the hemoglobin solution is cooled to about 2-8° C.

Example 11

Purification

The resulting solution is oxygenated by allowing the solution to stand under an oxygen atmosphere and is subsequently transferred to a purification system 42. The purification may be achieved by column chromatography, filtration, preferably membrane filtration (diafiltration), or a combination of filtration and column chromatography.

Figure 13:
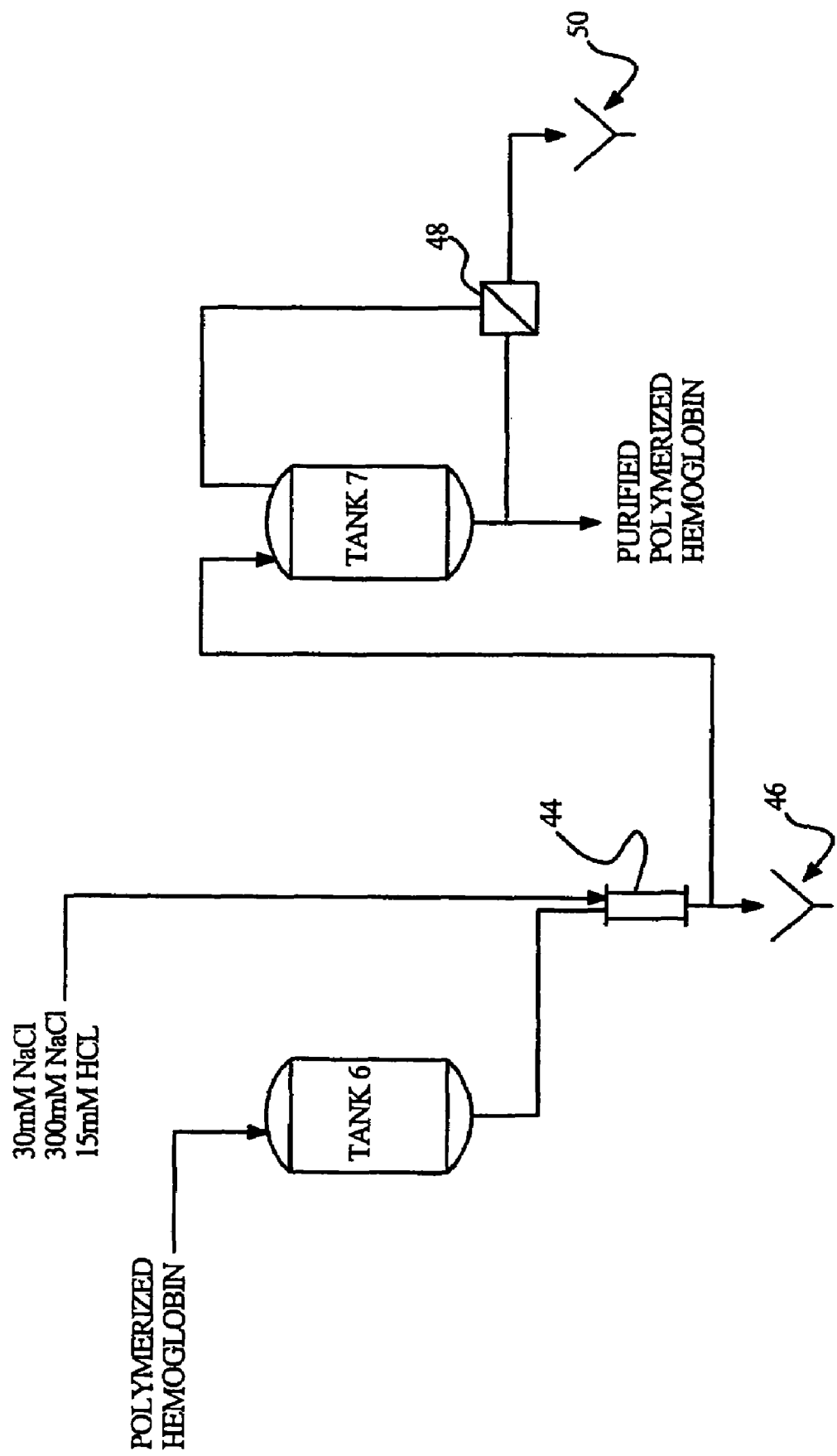
FIG. 13 is a schematic diagram depicting a column chromatography purification process employed in the invention.

In one embodiment, the solution is transferred to chromatography feed vessel, Tank 6, as shown in FIG. 13. In this embodiment, the resulting solution of oxyhemoglobin is then diluted to about 200 L (4% total hemoglobin) in Tank 6 and the concentration of chloride is adjusted to 22 mM with sodium chloride solution. No adjustment of sodium concentration is necessary.

Five 40 L aliquots of the resulting hemoglobin solution are then chromatographed using Column 44. Column 44 contains an affinity gel which is an agarose gel modified with a yellow dye (commercially available from Affinity Chromatography, Ltd., as Mimetic Yellow No. 1) having greater affinity for polymer than tetramer.

The chromatography is accomplished as follows. 40 L of oxygenated, polymerized, pyridoxylated, stroma-free hemoglobin solution is loaded onto Column 44. The column is washed with 15 column volumes (about 750 L) of 30 mM aqueous NaCl buffer to remove tetramer. The column is then washed with about 250 L of a 300 mM sodium chloride buffer to wash the polymer off. Polymer fractions are collected in Tank 7. Unwanted fractions are sent to drain 46. After each aliquot is removed, the column is regenerated with 15 mM HCL solution (150 L), re-equilibrated with 30 mM aqueous NaCl (250 L) and another aliquot of feed solution (40 L) is loaded to the column. The column is again washed with 30 mM NaCl followed by 300 mM NaCl. 40 L aliquots of hemoglobin solution are added to the column and chromatographed until Tank 6 is empty.

The collected fractions in Tank 7 are ultrafiltered (concentrated) using filter 48 associated with drain 50 to a volume of about 40 L (6% total hemoglobin). The concentrated hemoglobin solution is then transferred to gas exchange Tank 8 for deoxygenation.

Figure 14:
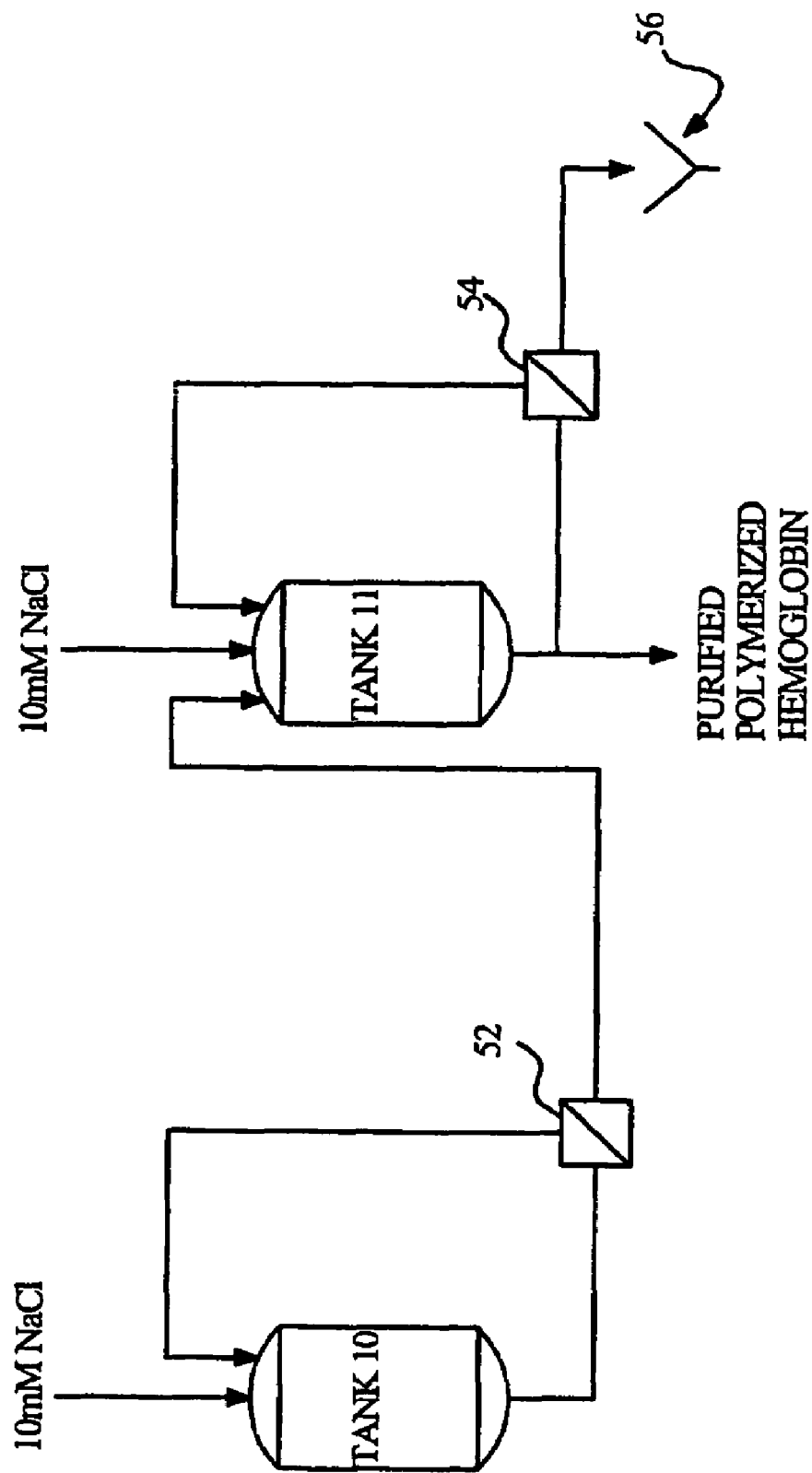
FIG. 14 is a schematic diagram depicting a membrane filtration purification process employed in the invention.

Alternatively, the solution is transferred to a filtration recycle vessel 10, as shown in FIG. 14. The hemoglobin is then diluted to about 4% THb in Tank 10. The 4% THb solution is then diafiltered using 10 mM NaCl and a 300,000 molecular weight filter 52 commercially available from Millipore Corporation. The filtration is continued until about 97% of the hemoglobin material passes through the filter and into Tank 11. (About 3% of the material, i.e., high molecular weight polymers, is retained in Tank 10). The amount of hemoglobin is determined spectrophotometrically using a cooximeter.

The resulting material in Tank 11 is about 4-8% THb and contains about 7-10% tetramer based on THb. The 4-8% THb is then diafiltered using 10 mM NaCl and a 100,000 molecular weight filter 54 commercially available from Pall-Filtron associated with drain or trap 56. The filtration is continued until the level of tetramer, as determined by size exclusion chromatography using a Toso BioSep 300×7.8 mm column, is less than 1.0% of the hemoglobin mass by weight. The resulting purified hemoglobin solution remains initially in Tank 11 and is subsequently transferred to gas exchange Tank 8 for deoxygenation.

Example 12

Deoxygenation

Gas exchange Tank 8 may be the same tank as Tank 4 or, preferably, a different tank. Gas exchange Tank 8 is equipped in essentially the same fashion as gas exchange Tank 4 and is attached to foam can 58 or equipped with a mechanical foam breaker in a fashion identical to that of Tank 4. Deoxygenation is accomplished in about 2.5 hours with a nitrogen sparge at about 10° C. and a solution pH of about 8.8. Nitrogen sparging is continued until less than about 16% oxyhemoglobin, based on the weight of total hemoglobin, remains in the solution. The resulting deoxyhemoglobin solution is subsequently transferred to Tank 9 for formulation.

If the heat treatment step of Example 10 has been postponed, it may be conducted at this stage. If heat treatment is conducted now, the purification procedures of Examples 11 and the deoxygenation procedures of this Example should be repeated. The heat treatment step of Example 10 and the heat treatment step at this point are optional and may be eliminated completely.

Example 13

Formulation

In formulation Tank 9, the solution is first concentrated to about 7% total hemoglobin, and the pH is adjusted to about 8.8 to 9.0 at 4° C. The pH is adjusted using 0.2 M NaOH. Glucose and glycine are added to achieve final concentrations of about 1 g/L and 3.5 g/L respectively. Potassium chloride is added to the solution to obtain a potassium concentration of about 3.5 to 4.5 mM. 3 M sodium chloride is then added to obtain an 85-110 mM chloride concentration. Sodium lactate is subsequently added to obtain a 135-155 mM concentration of sodium ion. Finally, a 0.45 molar ascorbic acid solution is added until the ascorbic acid concentration reaches about 1000 mg/L. The pH is adjusted to 8.7-9.1 at 10-15° C. using 0.22 M NaOH. The resulting hemoglobin solution has a final osmolality of about 280-360 mmole per kg.

The formulated hemoglobin solution is then concentrated to about 10% total hemoglobin using filter 60 associated with trap 62. The 10% hemoglobin solution is then sterilized by filtration through filter 64 and aseptically filled into presterilized bags.

Example 14

Solution Pre-Elaboration

Whether or not the solution has been subjected to the hot quench or optional heat treatment steps to elaborate tetramer during processing, the solution may be heated anytime after formulation to elaborate tetramer by heating the solution to about 45-55° C. for about 20-30hours, or until tetramer has increased above about 1-3%. Following heat treatment the solution should be purified as in Example 11 and degassed as in Example 13. Since the solution at this point has already been formulated, the additives introduced in Example 12 are preferably removed by diafiltration prior to purification, and then reintroduced during reformulation.

Example 15

Re-processing Aged Hemoglobin Solutions

Out of date or aged hemoglobin solutions may be reprocessed as in Example 14, without heat treating. Typically, hemoglobin solutions that are older than about 12-18 months at storage conditions of about 2-8° C. have tetramer levels of greater than about 1.0%. This material may be introduced to Tank 5 and purified and reformulated according to Examples 11-13. Since the solution at this point has already been formulated, the additives introduced in Example 13 are preferably removed by diafiltration prior to purification, and then reintroduced during re-formulation.

In the foregoing, there has been provided a detailed description of preferred embodiments of the invention for the purpose of illustration and not limitation. It is to be understood that all other modifications, ramifications and equivalents obvious to those having skill in the art based on this disclosure are intended to be within the scope of the invention as claimed.

What is claimed is:

1. A method for producing a substantially tetramer free hemoglobin solution comprising:
    a) polymerizing hemoglobin in solution;
    b) heat treating the polymerized hemoglobin in solution;
    c) removing tetramer from the polymerized hemoglobin in solution.

2. The method of claim 1 wherein the hemoglobin is derived from bovine blood.

3. The method of claim 1 wherein the hemoglobin is polymerized with glutaraldehyde.

4. The method of claim 1 wherein the tetramer is removed by filtration.

5. The method of claim 1 wherein the tetramer concentration at the completion of step (c) is less than about 1.0% of total hemoglobin in the solution.

6. The method of claim 1 wherein the tetramer concentration at the completion of step (c) is less than about 0.3% of total hemoglobin in the solution.

7. The method of claim 1 wherein the hemoglobin is derived from mammalian blood.

8. The method of claim 7 wherein the mammalian blood is human blood and the hemoglobin is pyridoxylated.

9. The method of claim 1 further comprising, in addition to step (c), removing tetramer from the solution prior to the heat treating.

10. The method of claim 9 wherein tetramer is removed from the solution prior to the heat treating until the solution is essentially tetramer free.

11. The method of claim 10 wherein the tetramer concentration prior to the heat treating is less than about 1.0% of total hemoglobin in the solution.

12. The method of claim 11 wherein the tetramer concentration prior to the heat treating is less than about 0.3% of total hemoglobin in the solution.

13. A method for stabilizing an essentially tetramer free polymerized hemoglobin solution comprising treating the polymerized hemoglobin solution to partially degrade the polymerized hemoglobin to tetramer and removing the tetramer from the solution.

14. The method of claim 13 wherein the treating comprises aging the solution.

15. The method of claim 13 wherein the treating comprises aging the solution until the tetramer concentration is above about 1.0% of the total hemoglobin in solution.

16. The method of claim 13 wherein the treating comprises heating the solution until the tetramer concentration is above about 1.0% of the total hemoglobin in solution.

17. The method of claim 13 wherein the hemoglobin is derived from mammalian blood.

18. The method of claim 13 wherein the mammalian blood is human blood and the hemoglobin is pyridoxylated.

19. The method of claim 13 wherein the hemoglobin is derived from bovine blood.

20. The method of claim 13 wherein the hemoglobin is polymerized with glutaraldehyde.

21. The method of claim 13 wherein the tetramer is removed by filtration.

22. The method of claim 13 wherein the treating comprises heating the solution.

23. The method of claim 22 wherein the heating comprises heating the solution above about 45° C. for at least about 24 hours.

24. A method for producing a stabilized, polymerized hemoglobin solution comprising:
 a) producing a polymerized hemoglobin solution;
 b) removing tetramer from the polymerized hemoglobin solution to produce a substantially tetramer free polymerized hemoglobin solution;
 c) aging the polymerized hemoglobin solution; and
 d) removing the elaborated tetramer.

25. The method of claim 24 wherein the aging comprises storing the hemoglobin solution until the tetramer concentration is greater than about 1.0% of total hemoglobin.

26. The method of claim 24 wherein the aging comprises storing the hemoglobin solution until the tetramer concentration is greater than about 3.0% of total hemoglobin.

27. The method of claim 24 wherein the aging comprises storing the hemoglobin solution for longer than one year.

28. A method for producing a substantially tetramer free hemoglobin solution comprising:
 e) subjecting hemoglobin in solution to a polymerization reaction comprising a polymerizing agent;
 f) quenching the polymerization reaction with a quenching agent;
 g) heating the solution during the quenching;
 h) removing tetramer from the polymerized hemoglobin in solution.

29. The method of claim 28 wherein the solution is heated to at least about 40° C. during the quenching for at least three hours.

30. The method of claim 29 wherein the solution is heat to about 40-50° C.

* * * * *